United States Patent [19]
Hargrave et al.

[11] Patent Number: 5,837,704
[45] Date of Patent: *Nov. 17, 1998

[54] 2-HETEROARYL-5,11-DIHYDRO-6H-DIPYRIDO[3,2-B:2',3'-E][1,4]DIAZEPINES AND THEIR USE IN THE PREVENTION OR TREATMENT OF HIV INFECTION

[75] Inventors: Karl Hargrave, Brookfield; John Proudfoot, Newtown; Usha Patel, Brookfield; Suresh Kapadia, Danbury; Terence Kelly, Ridgefield; Daniel McNeil, New Fairfield; Mario Cardozo, Brookfield, all of Conn.

[73] Assignee: Boehringer Ingelheim Pharmaceuticals, Inc., Ridgefield, Conn.

[ * ] Notice: This patent issued on a continued prosecution application filed under 37 CFR 1.53(d), and is subject to the twenty year patent term provisions of 35 U.S.C. 154(a)(2).

[21] Appl. No.: 663,162
[22] PCT Filed: Feb. 17, 1995
[86] PCT No.: PCT/US95/01993
§ 371 Date: Aug. 1, 1996
§ 102(e) Date: Aug. 1, 1996
[87] PCT Pub. No.: WO95/22545
PCT Pub. Date: Aug. 24, 1995

[51] Int. Cl.$^6$ .......... A61K 31/55; A61K 243/10; A61K 487/12; A61K 513/00
[52] U.S. Cl. .......... 514/220; 540/495; 540/557
[58] Field of Search .......... 540/495, 557; 514/220

[56] References Cited

U.S. PATENT DOCUMENTS 5,366,972 11/1994 Hargrave et al. .

OTHER PUBLICATIONS

Proudfoot et al., (Journal of Medicinal Chemistry, 1995, 38, 4830–4838.
K. Hargrave et al., "Novel Non-Nucleoside Inhibitors of HIV-1 Reverse Transcriptase. 1. Tricyclic Pyridobenzo- and Dipyridodiazepinones", *J. Med. Chem.*, 34, pp. 2231–2241 (1991).

*Primary Examiner*—Mukund J. Shah
*Assistant Examiner*—Bruck Kifle
*Attorney, Agent, or Firm*—Robert P. Raymond; Alan R. Stempel; Mary-Ellen Devlin

[57] ABSTRACT

Novel compounds for the treatment of HIV-1 infection. These are 2-heteroary-5,11-dihydro-6H-dipyrido[3,2-b:2',3'-e][1,4]diazepines of the formula

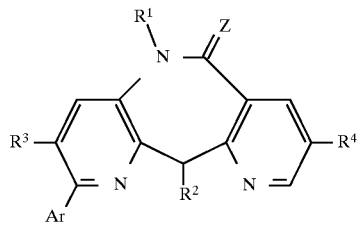

wherein Z is oxygen, sulfur, $=NCN$ or $=NOR^{10}$ and Ar is a group of the formula I, II, III, IV or V

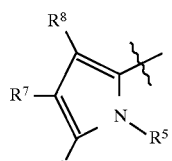

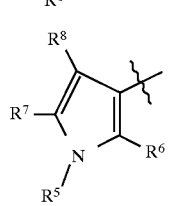

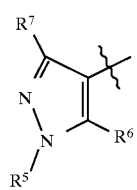

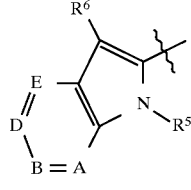

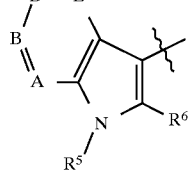

7 Claims, No Drawings

2-HETEROARYL-5,11-DIHYDRO-6H-DIPYRIDO[3,2-B:2',3'-E][1,4]DIAZEPINES AND THEIR USE IN THE PREVENTION OR TREATMENT OF HIV INFECTION

This application is a 371 of PCT/US95/01993, filed 17 Feb. 1995, which claims priority of U.S. application Ser. No. 08/198,242, filed 18 Feb. 1994.

FIELD OF THE INVENTION

The invention relates to novel 2-heteroaryl-5,11-dihydro-6H-dipyrido[3,2-b:2',3'-e][1,4]-diazepines and pharmaceutically acceptable salts thereof, methods for preparing these compounds, the use of these compounds either alone or in combination with other anti-virals, immunomodulators, antibiotics, anti-infectives, or vaccines in the prevention or treatment of HIV infection, and to pharmaceutical compositions containing these compounds.

BACKGROUND OF THE INVENTION

The human disease, Acquired Immune Deficiency Syndrome (AIDS), is caused by the Human Immunodeficiency Virus (HIV), particularly the strain known as HIV-1.

Like other viruses, HIV-1 cannot replicate without commandeering the biosynthetic apparatus of the host cell it infects. It causes this apparatus to produce the structural proteins which make up the viral progeny. These proteins are coded for by the genetic material contained within the infecting virus particle, or virion. Being a retrovirus, however, the genetic material of HIV is RNA, not DNA as in the host cell's genome. Accordingly, the viral RNA must first be converted into DNA, and then integrated into the host cell's genome, in order for the host cell to produce the required viral proteins. The conversion of the RNA to DNA is accomplished through the use of the enzyme reverse transcriptase (RT), which is included within the infecting virion along with the RNA. Reverse transcriptase has three known enzymatic functions; it acts as an RNA-dependent DNA polymerase, as a ribonuclease, and as a DNA-dependent DNA polymerase. Acting first as an RNA-dependent DNA polymerase, RT makes a single-stranded DNA copy of the viral RNA. Acting as a ribonuclease, RT frees the DNA just produced from the original viral RNA and destroys the original RNA. Finally, acting as a DNA-dependent DNA polymerase, RT makes a second, complementary DNA strand, using the first DNA strand as a template. The two strands form double-stranded DNA, which is integrated into the host cell's genome by another enzyme called integrase.

Compounds which inhibit the enzymatic functions of HIV-1 reverse transcriptase will inhibit replication of HIV-1 in infected cells.

A number of compounds that inhibit the enzymatic functions of HIV-1 reverse transcriptase are known. One class of known HIV-1 RT inhibitors is the nucleoside analogs. This class includes 3'-azido-3'-deoxythymidine (AZT), 2',3'-dideoxyinosine (ddI), and 2',3'-dideoxycytidine (ddC). Another class is the non-nucleoside analogs. This class includes, inter alia, nevirapine, which is 11-cyclopropyl-5,11-dihydro-4-methyl-6H-dipyrido[3,2-b:2',3'-e][1,4]diazepin-6-one. Nevirapine and other paricularly relevant compounds of the non-nucleoside class are described in U.S. Pat. No. 5,366,972; and by Hargrave et al. , "Novel Non-Nucleoside Inhibitors of HIV-1 Reverse Transcriptase. 1. Tricyclic Pyridobenzo- and Dipyridodiazepinones", *J. Med. Chem.*, 34, 2231 (1991).

OBJECT OF THE INVENTION

As with any anti-viral therapy, use of RT inhibitors in the treatment of HIV-1 infection tends to produce virus which is less sensitive to the given drug. Resistance (reduced sensitivity) to these drugs is the result of mutations which occur in the reverse transcriptase segment of the pol gene.

The object of the present invention is to provide improved, non-nucleoside inhibitors of HIV-1 RT which are more potent against mutant strains of HIV-1 than the known compounds of this class.

The compounds of the present invention satisfy this object in that they are highly potent against not only the wild-type (non-mutated) virus RT enzyme, but are also effective against the reverse transcriptase of many mutant viruses which have been observed in patients who have been treated with RT inhibitors. Specifically, the compounds of the present invention are effective in inhibiting the Y181C mutant [in which the tyrosine (Y) at codon 181 has been mutated to a cysteine (C) residue] which has been the most commonly observed mutant in clinical studies following therapy with many non-nucleoside reverse transcriptase inhibitors. The compounds are also effective against other observed mutant enzymes which contain a single point mutation such as Y188L, K103N, V106A, G190A, Y188C, or P236L.

SUMMARY OF THE INVENTION

A first aspect of the invention comprises novel 2-heteroaryl-dipyridodiazepines. These possess inhibitory activity against both wild-type and mutant HIV-1 RT. A second aspect of the invention comprises methods for making these novel compounds. A third aspect of the invention is a method for inhibiting replication of HIV-1 in a human host infected by HIV-1. A fourth aspect of the invention is a method for preventing or treating HIV-1 infection which comprises administering, to a human being exposed to or infected by HIV-1, a prophylactically or therapeutically effective amount of one of the above-mentioned novel compounds, either alone or in combination with other anti-viral agents, immunomodulators, antibiotics, anti-infectives, or vaccines. A final aspect of the invention comprises pharmaceutical compositions suitable for the prevention or treatment of HIV-1 infection comprising the above-mentioned compounds.

DESCRIPTION OF THE INVENTION

In one of its composition of matter aspects, the invention comprises 2-heteroaryl-5,11-dihydro-6H-dipyrido[3,2-b:2',3'-e][1,4]diazepines of the formula 1

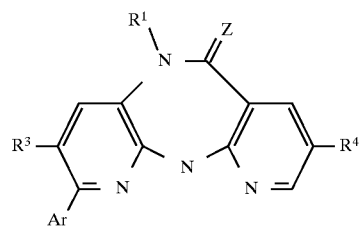

wherein,

Z is an oxygen or sulfur atom, =NCN or a group of the formula =NOR$^{10}$ wherein R$^{10}$ is alkyl of 1 to 3 carbon atoms;

R$^1$ is a hydrogen atom, alkyl of 1 to 3 carbon atoms, fluoroalkyl of 1 to 3 carbon atoms and 1 to 3 fluorine atoms, cyclopropyl, allyl, propargyl, 2-halo-2-propen-1-yl, mono- or dihalovinyl, alkanoyl or alkyl (thiocarbonyl) of 2 to 3 carbon atoms, alkylsulfonyl of 1 to 2 carbon atoms, mono- or di-alkylaminocarbonyl wherein the alkyl moiety contains 1 to 2 carbon atoms, aminoethyl, mono- or di-alkylaminoethyl wherein the alkyl moiety contains 1 to 2 carbon atoms, alkyloxyalkyl or alkylthioalkyl of 2 to 3 carbon atoms, or cyanoalkyl wherein the alkyl moiety contains 1 to 2 carbon atoms;

$R^2$ is a hydrogen atom, alkyl of 1 to 4 carbon atoms, fluoroalkyl of 1 to 4 carbon atoms and 1 to 3 fluorine atoms, cycloalkyl of 3 to 6 carbon atoms, oxetanyl, thietanyl, tetrahydrofuranyl, tetrahydrothienyl, tetrahydropyranyl, tetrahydrothiopyranyl, alkenylmethyl or alkynylmethyl of 3 to 4 carbon atoms, alkyloxyalkyl or alkylthioalkyl of 2 to 3 carbon atoms, alkanoyl or alkyl(thiocarbonyl) of 2 to 5 carbon atoms, or cyanoalkyl of 2 to 3 carbon atoms;

$R^3$ is a hydrogen atom, methyl or a halogen atom;

$R^4$ is a hydrogen atom, hydroxy, amino, hydroxymethyl, or aminomethyl; and,

Ar is a group of the formula I, II, III, IV or V

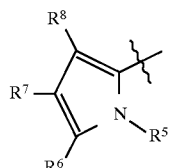  I

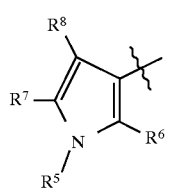  II

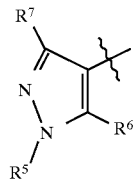  III

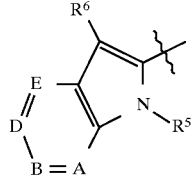  IV

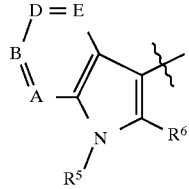  V wherein, $R^5$ is hydrogen, methyl, ethyl, acetyl, aminocarbonyl, (N-alkyl)aminocarbonyl, or (N,N-dialkyl) aminocarbonyl, wherein the alkyl moieties each contain one to two carbon atoms;

$R^6$, $R^7$ and $R^8$ are each hydrogen; or, one of $R^6$, $R^7$ and $R^8$ is methyl, ethyl, hydroxymethyl, hydroxyethyl, trifluoromethyl, halogen, acetyl, methoxycarbonyl, ethoxycarbonyl, carboxy, mono- or dimethylaminosulfonyl, aminosulfonyl, mono- or dimethylaminocarbonyl, aminocarbonyl, methyl- or ethylsulfinyl, methyl- or ethylsulfonyl, cyano, or nitro, and the remaining two substituents are both hydrogen;

A, B, D, and E are each methine groups, one of which may optionally be substituted with $R^9$; or, one of A, B, D, and E is a nitrogen atom, and the remaining three of A, B, D, and E are each methine groups, one of which methine groups may optionally be substituted with $R^9$; and, $R^9$ is alkyl or alkyloxy of 1 to 3 carbon atoms, amino, mono- or dimethylamino, hydroxyl, methylsulfonylamino, acetylamino, acetyloxy, aminocarbonyl, mono- or dimethylaminocarbonyl, or halogen.

A subgeneric aspect of the invention comprises compounds of formula 1, wherein,

Z is an oxygen or sulfur atom, or a group of the formula $=NOR^{10}$ wherein $R^{10}$ is methyl or ethyl;

$R^1$ is a hydrogen atom, alkyl of 1 to 3 carbon atoms, or allyl;

$R^2$ is alkyl of 1 to 3 carbon atoms or cycloalkyl of 3 to 4 carbon atoms;

$R^3$ is a hydrogen atom, methyl, chloro, or bromo;

$R^4$ is a hydrogen atom;

Ar is a group of the formula I, II, III, IV or V, wherein, $R^5$ is hydrogen, methyl or ethyl;

$R^6$, $R^7$ and $R^8$ are each hydrogen; or, one of $R^6$, $R^7$ and $R^8$ is methyl, ethyl, hydroxymethyl, hydroxyethyl, trifluoromethyl, halogen, acetyl, methoxycarbonyl, ethoxycarbonyl, mono- or dimethylaminosulfonyl, aminosulfonyl, mono- or dimethylaminocarbonyl, aminocarbonyl, methyl- or ethylsulfinyl, methyl- or ethylsulfonyl, cyano, or nitro, and the remaining two substituents are both hydrogen;

A, B, D, and E are each methine groups, one of which may optionally be substituted with $R^9$; or, one of A, B, D, or E is a nitrogen atom, and the remaining three of A, B, D, and E are each methine groups, one of which methine groups may optionally be substituted with $R^9$; and, $R^9$ is alkyl or alkyloxy of 1 to 3 carbon atoms, amino, hydroxyl, or halogen.

A particular subgeneric aspect of the invention comprises compounds of formula 1 wherein, Z is an oxygen or sulfur atom;

$R^1$ is methyl;

$R^2$ is alkyl of 2 to 3 carbon atoms, or cycloalkyl of 3 to 4 carbon atoms;

$R^3$ and $R^4$ are each hydrogen atoms;

Ar is a group of the formula I, II or III, wherein, $R^5$ is hydrogen or methyl;

$R^6$, $R^7$ and $R^8$ are each hydrogen; or, one of $R^6$, $R^7$ and $R^8$ is methyl, trifluoromethyl, acetyl, methoxycarbonyl, ethoxycarbonyl, or cyano, and the remaining two substituents are both hydrogen; or, Ar is a group of the formula IV or V, wherein, $R^5$ is hydrogen or methyl;

$R^6$, $R^7$ and $R^8$ are each hydrogen, or one of $R^6$, $R^7$ and $R^8$ is methyl and the remaining two substituents are both hydrogen;

A, B, D, and E are each methine groups, one of which may optionally be substituted with $R^9$; or, one of A, B, D, or E is a nitrogen atom, and the remaining three of A, B, D, and E are each methine groups, one of which methine groups may optionally be substituted with $R^9$; and, $R^9$ is hydrogen, alkyl or alkyloxy of 1 to 3 carbon atoms, amino, hydroxyl, or halogen.

Preferred compounds of formula I are:

5,11-Dihydro-11-ethyl-5-methyl-2-(3-pyrrolyl)-6H-dipyrido[3,2-b:2',3'-e][1,4]diazepin-6-one;

11-Cyclopropyl-5,11-dihydro-5-methyl-2-(3-pyrrolyl)-6H-dipyrido[3,2-b:2',3'-e][1,4]diazepin-6-one;

11-Cyclopropyl-5,11-dihydro-5-methyl-2-(4-pyrazolyl)-6H-dipyrido[3,2-b:2',3'-e][1,4]diazepin-6-one; and, 5,11-Dihydro-11-ethyl-5-methyl-2-(4-pyrazolyl)-6H-dipyrido[3,2-b:2',3'-e][1,4]diazepin-6-one.

Synthesis Of Compounds Of Formula 1 And Their Salts

The compounds of Formula 1 and their salts can be prepared by known methods or obvious modifications thereof, in accordance with the general synthetic scheme shown below. According to one alternative offered by this synthetic scheme, compounds of the general formulas 2A, 2B, 2C or 2D (wherein Z is, respectively oxygen, sulfur, =NCN or =NOR$^{10}$) undergo aryl-aryl coupling, to yield corresponding 2-aryl substituted compounds according to the invention of formulas 1A, 1B, 1C or 1D. According to the other alternative offered by the scheme, a compound of the general formula 2A is converted to a 2-aryl compound of the formula 1A, and the resulting compound, wherein Z is oxygen, can then be converted, as desired, into a compound of formula 1B, 1C or 1D, wherein Z is, respectively, sulfur, =NCN or =NOR$^{10}$. Several methods for performing aryl-aryl coupling are illustrated below. These methods are generally known from, for example, J. K. Stille, *Angew. Chem., Int. Ed Engl.*, 25,508 (1986); A. M. Echavarren and J. K. Stille, *J. Am. Chem. Soc.*, 109, 5478 (1987); V. Farina and B. Krishnan, *J. Am. Chem. Soc.*, 113, 9585 (1991); and R. F. Heck, *Acc. Chem. Res.*, 12, 146 (1979). Although not illustrated below, another general method for performing such aryl-aryl coupling, the Suzuki reaction, makes use of arylboronic acids in the presence of palladium-based catalysts and is exemplified, for example, in N. M. Ali, A. McKillop, M B. Mitchell, R. A. Rebelo, and P. J. Wallbank, *Tetrahedron*, 48, 8117 (1992). Methods for the preparation of compounds of formulas 2A, 2B, 2C and 2D are generally known from published European Patent Application 0 429 987 and U.S. Pat. No. 5,366,972, but are also described in detail below. Similarly, methods for converting a compound of the formula 1A into one of formula 1B, 1C or 1D, described below, are obvious variations of methods already taught in European Patent Application 0 429 987 and U.S. Pat. No. 5,366,972.

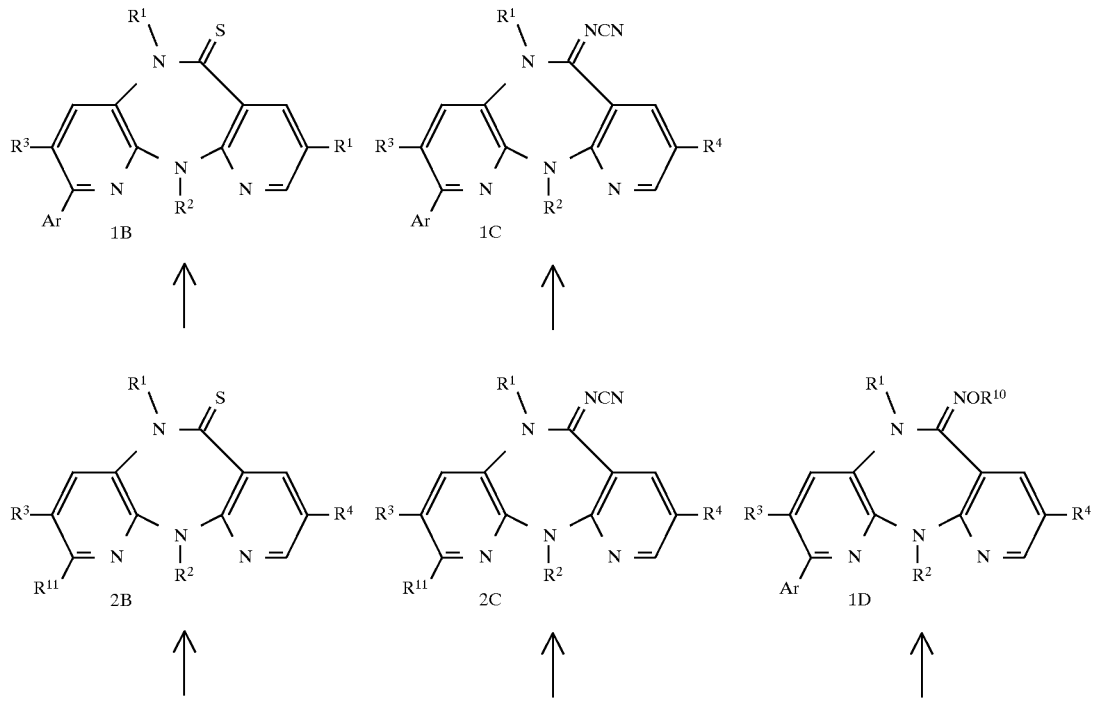

-continued

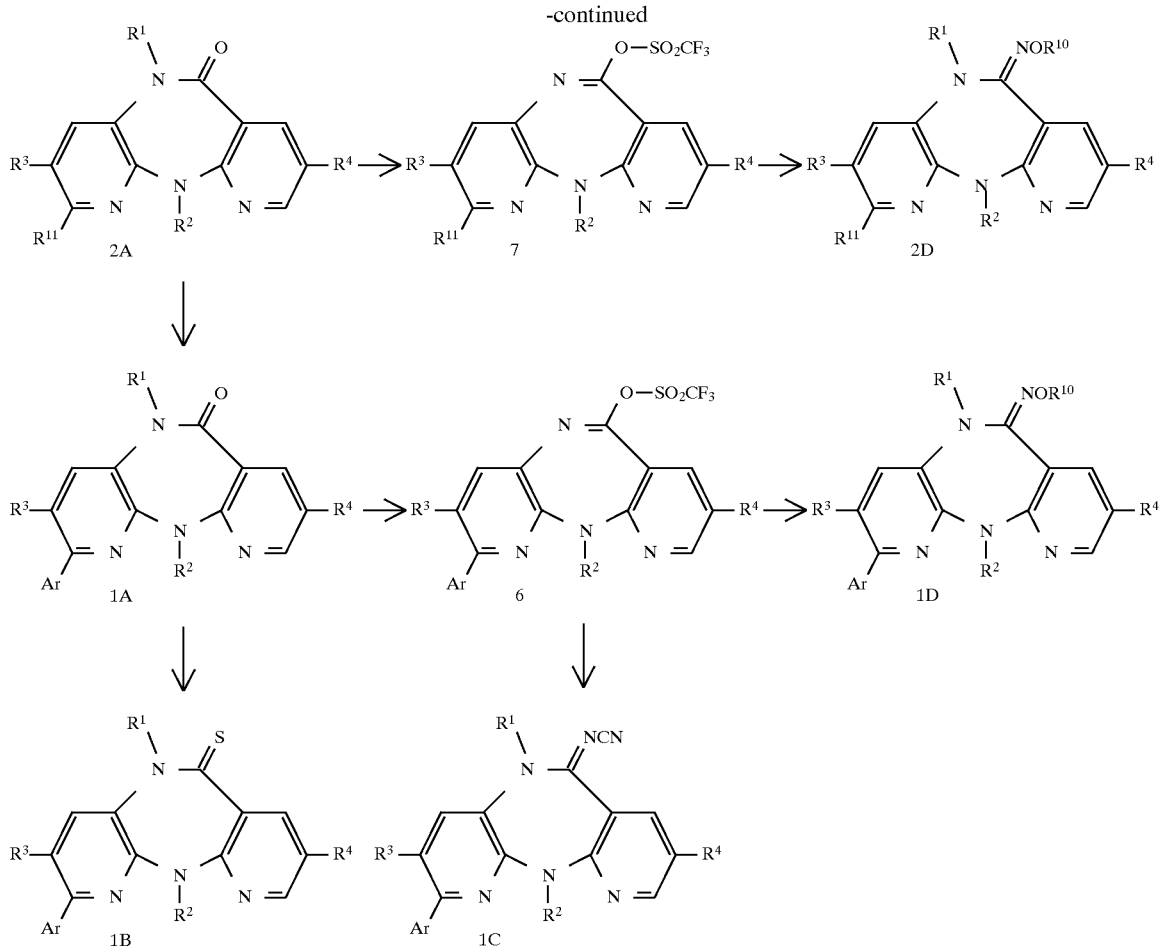

Method A

Compounds of formula 1A or 1B

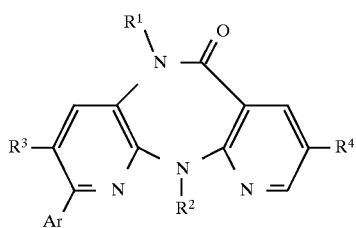

wherein Ar, and $R^1$ through $R^4$ are as defined above, may be obtained by condensing compounds of formula 2A or 2B

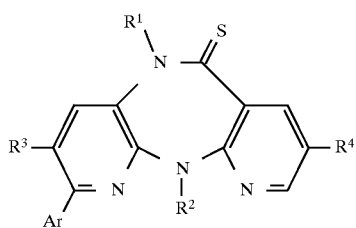

wherein $R^1$ through $R^4$ are as defined above and $R^{11}$ is a leaving group, for instance chloro, bromo, iodo or $-OSO_2CF_3$, with tributyltin compounds of formula 3, $$Ar-SnBu_3 \quad 3$$

wherein Ar is as defined above, in the presence of a catalyst, preferably a palladium catalyst such as tetrakis(triphenylphosphine)palladium(0), tetrakis(triphenylarsine)

palladium(0), tetrakis(tri-2-furylphosphine)palladium(0), or bis(triphenylphosphine)palladium(II) chloride. These reactions are generally carried out under an inert atmosphere of argon or nitrogen, and in inert solvents such as 1,4-dioxane, tetrahydrofuran, N,N-dimethylformamide, N-methylpyrrolidinone, and the like, at temperatures generally between room temperature and the boiling point of the solvent. In some cases, the trimethyl tin compounds corresponding to the tributyltin compounds of formula 3 may be used.

Method B

In an alternative method, compounds of formula 1A or 1B, wherein Ar, and $R^1$ through $R^4$ are as defined above, may be obtained by condensing compounds of the formula 2A or 2B, wherein $R^1$ through $R^4$ and $R^{11}$ are as defined above, with organozinc compounds of the formula 4

                                       4 which are obtainable by adding zinc chloride to the organolithium compound of the formula 5

                                       5 wherein Ar is as defined above. These reactions are generally carried in a manner analogous to Method A, i.e., under an inert atmosphere such as argon or nitrogen, and in the presence of a palladium catalyst, such as tetrakis (triphenylphosphine)palladium(0), tetrakis(triphenylarsine) palladium(0), tetrakis(tri-2-furylphosphine)palladium(0), or bis(triphenylphosphine)palladium(II) chloride. Inert solvents such as 1,4-dioxane, tetrahydrofuran, ether, and the like are generally used, and the reaction temperatures are generally between room temperature and the boiling point of the solvent.

Method C

A compound of formula 1B can be obtained by reacting a compound of formula 1A with a sulfurating agent, such as 2,4-bis(4-methoxyphenyl)-1,3-dithia-2,4-diphosphetane-2, 4-disulfide; bis(tricyclohexyltin)sulfide; bis(tri-n-butyltin) sulfide; bis(tri-phenyltin)sulfide; bis(tri-methylsilyl)sulfide or phosphorous pentasulfide. The reaction is carried out in an inert organic solvent such as carbon disulfide, benzene or toluene, at room temperature or higher, preferably at an elevated temperature up to the boiling point of the reaction mixture, and preferably under anhydrous conditions. When using the above mentioned tin or silyl sulfides, it is preferable to carry out the sulfurization reaction in the presence of a Lewis acid such as boron trichloride.

Method D

Compounds of formula 1C

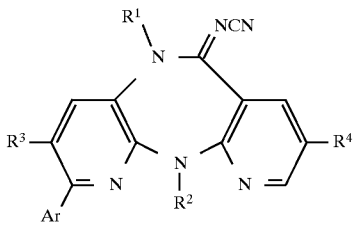

wherein $R^1$ is hydrogen, Ar and $R^2$ through $R^4$ are as defined above, can be obtained in two steps. In the first step a compound of the formula 1A, wherein $R^1$ is hydrogen, is reacted with trifluoromethanesulfonic anhydride to yield a compound of the formula 6.

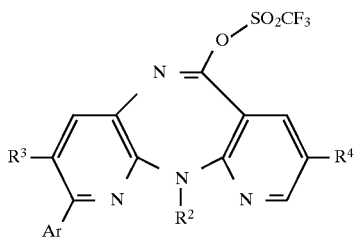

The reaction is preferably carried out in an inert solvent using one to two equivalents of trifluoromethanesulfonic anhydride and in the presence of one to two equivalents of a base. The base may be, for example, a tertiary amine such as triethylamine or diisopropylethylamine, and the inert solvent used may include, for example, methylene chloride, chloroform, diethylether, tetrahydrofuran, or toluene. Addition of the reagents is generally carried out at or below ambient temperature, and the mixture is then allowed to react, at or near room temperature. The alkoxyamine starting materials may be purchased or are known from the literature or may be obtained by procedures known from the literature. In the second step, the intermediate of formula 6 is reacted with cyanamide. This reaction is carried out in the presence of a base such as potassium carbonate, sodium carbonate, triethylamine, or diisopropylethylamine, and in an inert solvent such as methylene chloride, 1,4-dioxane, tetrahydrofuran, diethylether, chloroform, or dimethylformamide at a temperature between 0° C. up to the boiling point of the reaction mixture.

Compounds of formula 1C wherein $R^1$ is other than hydrogen can be obtained by producing a compound of formula 1C wherein $R^1$ is hydrogen, as described above, and then replacing the hydrogen with another substituent, as described below in Method K.

Method E

Compounds of formula 1D

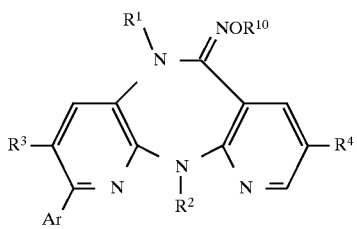

wherein $R^1$ is hydrogen, Ar and $R^2$ through $R^4$ are as defined above, can be obtained, in a manner analogous to that of Method D, by reacting a compound of formula 6, wherein Ar and $R^2$ through $R^4$ are as defined above with the appropriate alkoxylamine(O-alkylhydroxylamine) or their salts (for example, methoxyamine hydrochloride). The reaction is carried out under conditions analogous to those described for the treatment of compounds of formula 6 with cyanamide.

Compounds of formula 1D wherein $R^1$ is other than hydrogen can be obtained by producing a compound of formula 1D wherein $R^1$ is hydrogen, as described above, and then replacing the hydrogen with another substituent, as described below in Method K.

Method F

A compound of the formula 2A can be converted into a compound of the formula 2B

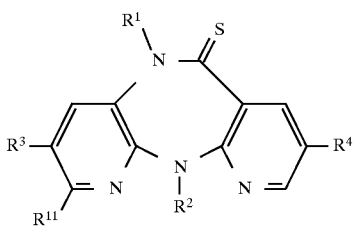

2B by sulfurization, in a manner analogous to that described above in Method C. In turn, the resulting compound of formula 2B can undergo aryl-aryl coupling, in a manner analogous to those described in methods A or B, to yield a compound of the formula 1B.

Method G

In a manner analogous to that described in Method D, a compound of the formula 2A can be converted to a compound of the formula 7

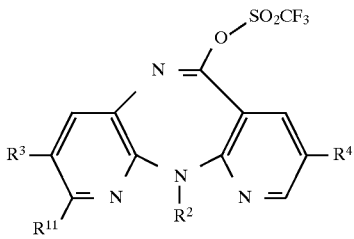

7 by treatment of the compound of formula 2A with trifluoromethanesulfonic anhydride. In turn, the compound of the formula 7 can be reacted with cyanamide to yield the final product of formula 1C, wherein $R^1$ is hydrogen.

Compounds of formula 1C wherein $R^1$ is other than hydrogen can be obtained by producing a compound of formula 1C wherein $R^1$ is hydrogen, as described above, and then replacing the hydrogen with another substituent, as described below in Method K.

Method H

In a manner analogous to that described in Method E, a compound of the formula 1D, wherein $R^1$ is hydrogen, can be obtained by reacting a compound of formula 7 with an appropriate alkoxylamine(O-alkylhydroxylamine) or its salt (for example, methoxylamine hydrochloride).

Compounds of formula 1D wherein $R^1$ is other than hydrogen can be obtained by producing a compound of formula 1D wherein $R^1$ is hydrogen, as described above, and then replacing the hydrogen with another substituent, as described below in Method K.

Preparation of Starting Materials of Formula 2A

As mentioned before, compounds of the formula 2A, can be obtained by known methods already described in EP-A-0 429 987 or U.S. Pat. No. 5,366,972, or obvious modifications thereof Methods I through L, described below, are illustrative of the methods for preparing such compounds.

Method I

Compounds of the formula 2A

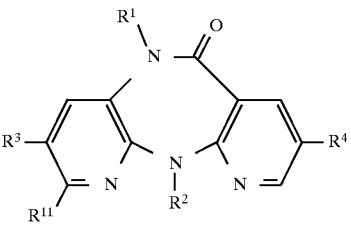

2A wherein $R^1$, $R^2$, $R^3$ and $R^4$ are as described above and $R^{11}$ is chloro, bromo, iodo or methoxy, can be obtained by cyclizing appropriate carboxylic acid amides of the formula 9

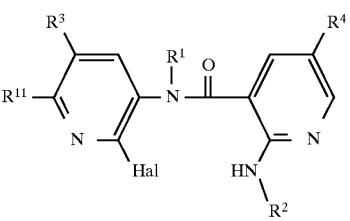

9 wherein $R^1$ through $R^4$ and $R^{11}$ are as defined above and Hal represents chlorine, bromine, fluorine or iodine.

A variant of this method, which is preferably used to prepare compounds of formula 2A wherein $R^4$ is an electron withdrawing group, involves cyclizing carboxylic acid amides of formula 9A,

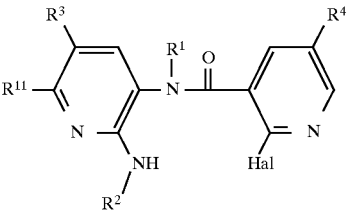

9A wherein $R^1$ through $R^4$, $R^{11}$ and Hal are defined as above with respect to compounds of formula 9.

Cyclization is conveniently carried out by the conversion of compounds of formula 9 or 9A into their alkaline metal salts and subsequent condensation at temperatures between 0° C. and the boiling point of the reaction mixture. If, in the starting compounds of formula 9 or 9A, $R^1$ is different from hydrogen, metallation requires at least 1 mole of the metallating agent. If, on the other hand, $R^1$ is hydrogen, at least 2 moles of this agent must be used. For metallation, lithium, sodium and potassium hydrides or lithium alkyls, such as n-butyl lithium, are preferably used.

The cyclization reaction is usually carried out in inert solvents, e.g. in tetrahydrofuran, 1,4-dioxane, glycoldimethyl ether, diethylene-glycoldimethyl ether, triethyleneglycoldimethyl ether, dimethylformamide, benzene or anisole. Cyclization may also be effected by heating carboxylic acid amides of formula 9 or 9A in dipolar aprotic solvents, preferably in sulfolane or dimethylsulfone. Catalytic quantities of strong acids, e.g. sulfuric acid, hydrochloric acid, hydrobromic acid, phosphoric acid, polyphosphoric acid, methanesulfonic acid or p-toluenesulfonic acid, have proved to be of use. The necessary reaction temperature is usually between 110° and 220° C.

To obtain a compound of the formula 2A wherein $R^{11}$ is —$OSO_2CF_3$ (a "triflate"), it is first necessary to produce a compound wherein $R^{11}$ is methoxy. The resulting intermediate is then demethylated by treatment with an appropriate acid, such as, for example, concentrated HBr or BBr$_3$. The resulting hydroxy intermediate is then converted to the triflate by treatment with trifluoromethanesulfonic anhydride (triflic anhydride), generally in the presence of a weak base, such as, for example, N,N-diisopropylethylamine or triethylamine.

The carboxylic acid amides of formula 9, used as starting materials, are obtained, for example, by amination of 2-chloro-nicotinic acid amides of formula 10

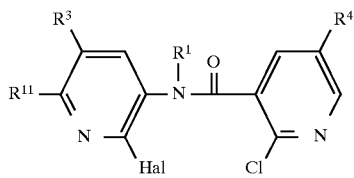

wherein $R^1$, $R^3$, $R^4$, $R^{11}$ and Hal are as hereinbefore defined, with primary amines of formula 11

 (11)

wherein $R^2$ is as hereinbefore defined. The reaction can also be carried out in the presence of inorganic or organic auxiliary bases, such as triethylamine, N,N-dimethylaniline, or sodium or potassium carbonate. The reaction can be carried out without using a solvent; it is of some advantage, however, to use inert organic solvents at temperatures of between 0° C. and 175° C., preferably at reflux temperature. Suitable inert solvents that can be used include an excess of the primary amine of general formula 11, open chain or cyclic ethers, such as tetrahydrofuran, 1,4-dioxane, glycoldimethyl ether, diethyleneglycoldimethyl ether; aromatic hydrocarbons, such as benzene, toluene, xylene, chlorobenzene or pyridine; alcohols such as methanol, ethanol, isopropanol; dipolar aprotic solvents such as dimethylformamide; 1,3-dimethyl-2-imidazolidinone, 1,3-dimethyl-tetrahydro-2(1H)-pyrimidinone and sulfolane.

Carboxylic acid amides of formula 9A can be prepared by condensation of an appropriately substituted 2-chloronicotinic acid chloride with an appropriately substituted 3-amino-2-(alkylamino)pyridine, under well known reaction conditions.

Intermediates of formula 10, wherein $R^1$ is different from hydrogen, can be prepared from 2-chloronicotinic acid amides of formula 12

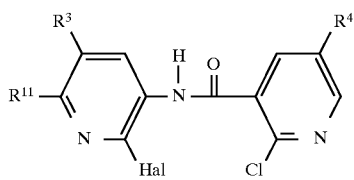

by reaction with alkylating agents of formula 13

 (13)

wherein $R^1$ is as defined above and X is an appropriate leaving group, for instance X stands for the radical of a reactive ester, a halogen atom, the group $OSO_2OR^1$, the methanesulfonyloxy or ethanesulfonyloxy group or an aromatic sulfonyloxy group, in the presence of proton acceptors, for example of amines, such as triethylamine, diazabicycloundecene, 4-(dimethylamino)pyridine, or alkali or alkaline earth metal hydroxides, such as sodium hydroxide, potassium hydroxide, calcium hydroxide, of alkali carbonates, or alkaline earth metal carbonates or hydrogen carbonates, such as sodium carbonate or potassium carbonate, or potassium hydrogen carbonate.

2-Chloronicotinic acid amides of general formula 12 can be obtained by condensation of an appropriately substituted 2-chloronicotinic acid chloride with an appropriately substituted 3-amino-2-halopyridine, under well known reaction conditions.

All the other starting materials needed to prepare compounds of the formula 2A are known from the literature or may be purchased or may be obtained by procedures known from the literature.

This method is not preferred when preparing compounds wherein $R^2$ is hydrogen, as it entails the use of ammonia, an inconvenient reactant. Method J, described below, is preferred when making compounds wherein $R^2$ is hydrogen.

Method J

Compounds of the formula 2A wherein wherein $R^1$, $R^3$, $R^4$ and $R^{11}$ are as defined above and $R^2$ is hydrogen, can be prepared by hydrolytic cleavage of the arylmethyl group in compounds of formula 14,

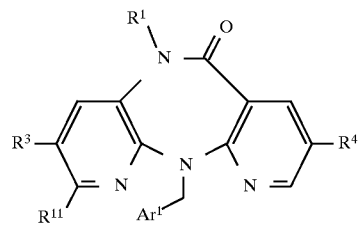

wherein $R^1$, $R^3$, $R^4$ and $R^{11}$ are defined as above and $Ar^1CH_2$ is a readily removable protecting group, for example, a benzyl or 4-methoxybenzyl group. Hydrolysis is effected by moderate to strong acids or Lewis-acids at temperatures between −20° and +150° C. Such acids can be, for example, sulfuric acid, methanesulfonic acid, trifluoroacetic acid, trifluoromethanesulfonic acid, phosphoric or polyphosphoric acid. When using phosphoric or polyphosphoric acid, the addition of solvents such as benzene, toluene, phenol, anisole or veratrole has proved to be of advantage.

If Lewis acids, such as aluminum chloride or bromide are used to eliminate the arylmethyl group, solvents such as aromatic hydrocarbons, e.g. benzene, toluene, anisole, or mixtures thereof with dichloromethane are suitable.

It will be obvious to those skilled in the art that this method is not preferred in those cases wherein $R^1$, $R^2$ or $R^4$ is readily hydrolyzable, for example, wherein $R^1$ is alkanoyl. In such cases it is preferable to use an alternative synthetic method.

Intermediates of formula 14 can be prepared by the condensation of appropriately substituted compounds of formulas 9 or 9A, in a manner analagous to those described in Method I.

Method K

A compound of the formula 2A wherein $R^1$ through $R^4$ and $R^{11}$ are as defined above, except that $R^1$ is not hydrogen, may be obtained by converting a compound of the formula 15

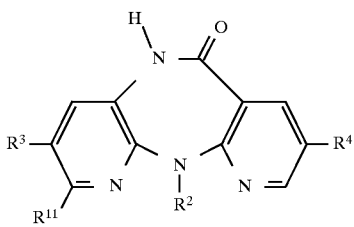

15 wherein $R^2$, $R^3$, $R^4$ and $R^{11}$ are defined as above, into the corresponding 5-alkali or alkaline earth metal compound and subsequently reacting the alkali metal compound with a compound of the formula 13

wherein $R^1$ is as defined above and X is an appropriate leaving group, for instance X stands for the radical of a reactive ester, a halogen atom, the group $OSO_2OR^1$, the methanesulfonyloxy or ethanesulfonyloxy group or an aromatic sulfonyloxy group. Instead of converting the compound of the formula 15 into its corresponding alkali metal salt in the first step, the alkylation of a compound of formula 15 may also be performed by reaction with a compound of formula 13 in the presence of amines, such as triethylamine, diazabicycloundecene or 4-(dimethylamino)pyridine, or of alkali carbonates or bicarbonates, such as sodium and potassium carbonate or sodium bicarbonate.

The conversion of a compound of formula 15 into the corresponding alkali metal or alkaline earth metal compound may be effected by reacting a compound of formula 15 with an alkali metal or alkaline earth metal hydroxide, such as lithium hydroxide, barium hydroxide, sodium hydroxide or potassium hydroxide, with an alkali metal alkoxide, such as sodium methoxide or potassium tert-butoxide, with an alkali metal amide, such as sodium amide or potassium amide, or with an alkali metal hydride such as sodium hydride or potassium hydride. The reaction is generally carried out in the presence of a suitable organic solvent at temperatures between −78° C. and +60° C., preferably at room temperature. Inert organic solvents, such as dimethylformamide, dimethylsulfoxide, tetrahydrofuran, glycoldimethyl ether, toluene, or pyridine are preferred if alkali metal hydrides are used as the metallating agents, whereas, if an alkali or alkaline earth metal hydroxide is used, an aqueous mixture with an organic solvent, such as methanol or tetrahydrofuran, may also be employed. For conversion of the alkali or alkaline earth metal-substituted 5,11-dihydro-6H-dipyrido[3,2-b:2',3'-e][1,4]diazepin-6-one thus obtained into a compound of general formula 2A, the solution or suspension of the alkali or alkaline earth metal compound is reacted directly, i.e. without isolation, with a compound of formula V at −20° C. or at elevated temperatures, up to the boiling point of the solvent or reaction medium, whichever is lower. The substitution takes place almost exclusively at the nitrogen atom in the 5-position of the dihydro-dipyridodiazepinone, even if $R^2$ in the starting material of formula 15 is a hydrogen atom, provided that one equivalent of base and one equivalent of a compound of formula 13 are used.

It will be obvious to those skilled in the art that the presence of nucleophilic substituents in the compounds of formula 2A may require the use of an intermediate of formula 2A having substituents which are, other than the 11-position nitrogen, not nucleophilic but which can be derivatized to yield the required group. For example, amino at $R^4$ is preferably obtained by alkylating or acylating an intermediate of formula 2A having a nitro group at $R^4$, and subsequently reducing the nitro group to yield the desired compound.

Intermediates of formula 15 can be obtained by the cyclization of appropriately substituted compounds of formulas 9 or 9A. This method is preferred in cases wherein cyclization would be impaired if $R^1$ were other than hydrogen.

Method L

A compound of the formual 2A, wherein $R^1$ through $R^4$ and $R^{11}$ are as defined above and $R^2$ is other than hydrogen, can be obtained by converting a 5,11-dihydro-6H-dipyrido[3,2-b:2',3'-e][1,4]diazepin-6-one of formula 2A, wherein $R^2$ is hydrogen, into the corresponding metal salt of formula 16A or—in the case of $R^1$ being hydrogen—into a compound of formula 16B

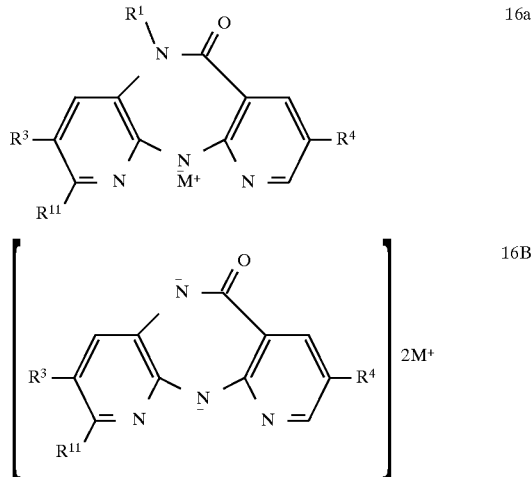

wherein M represents an alkali metal, such as lithium, sodium, potassium, rubidium or cesium, or M represents the group MgHal+, wherein Hal is a chlorine, bromine or iodine atom, and subsequently alkylating with a compound of formula 17

wherein $R^2$ and X are as hereinbefore defined.

The conversion of the intermediate compound of formula 2A into the corresponding alkali metal compound of formulae 16A or 16B may be effected by reacting a compound of formula 2A, wherein $R^2$ is hydrogen, with a lithium alkyl (e.g. n-butyl lithium, or t-butyl lithium) optionally in the presence of tetramethylethylenediamine, a lithium dialkylamide, (e.g. lithium diisopropylamide, lithium dicyclohexylamide and lithium isopropyl-cyclohexylamide), a lithium aryl (e.g. phenyl lithium), an alkali metal hydroxide (e.g. lithium, sodium or potassium hydroxide), an alkali metal hydride (e.g. sodium or potassium hydride), an alkali metal amide (e.g. sodium or potassium amides) or a Grignard reagent (e.g. methyl magnesium iodide, ethyl magnesium bromide or phenyl magnesium bromide). One equivalent of base is required for the formation of compounds of formula 16A, whereas two equivalents of base are required for the formation of compounds of formula 16B. The metallation is conveniently carried out in an inert organic solvent at temperatures of between −78° C. and the boiling point of the reaction mixture in question. If a lithium alkyl, lithium aryl, lithium dialkylamide or Grignard reagent is used for the metallation, the preferred solvents are ethers such as tetrahydrofuran, diethyl ether or dioxane, optionally in a mixture with aliphatic or aromatic hydrocarbons, such as hexane or benzene, and the operation may be carried out at temperatures of between −20° and +80° C. When metallation is effected with an alkali metal hydride or alkali metal amide, in addition to the solvents mentioned hereinbefore it is also possible to use xylene, toluene, acetonitrile, dimethylformamide and dimethylsulfoxide, while if an alkali metal hydroxide is used it is also possible to use alcohols such as ethanol, methanol and aliphatic ketones such as acetone, as well as mixtures of these solvents with water.

For conversion of the alkali metal salt thus obtained into a compound of formula 2A, wherein $R^2$ is other than hydrogen, the solution or suspension of the alkali metal compound is reacted directly, i.e. without isolation of the reaction product, with a compound of formula 17 at temperatures of between −20° and the boiling point of the reaction mixture, preferably at room temperature.

Formation Of Salts And Other Derivatives

Compounds of formula 1 may, if desired, be converted into their non-toxic, pharmaceutically acceptable addition salts by conventional methods; for example, by dissolving a compound of formula 1 in a suitable solvent and treating the solution with one or more molar equivalents of the desired acid or base, as appropriate. The invention also comprises such salts.

Examples of inorganic and organic acids which may form nontoxic, pharmaceutically acceptable acid addition salts with a compound of the formula 1 are the following: hydrochloric acid, hydrobromic acid, sulfuric acid, phosphoric acid, nitric acid, methanesulfonic acid, tartaric acid, fumaric acid, acetic acid, and the like. Examples of inorganic and organic bases which may form nontoxic, pharmaceutically acceptable basic addition salts with a compound of the formula 1 are the following: sodium hydroxide, potassium hydroxide, magnesium hydroxide, ammonia, tromethamine, and the like. Compounds of formula 1 may form addition salts with one molar equivalent of the acid or base, as appropriate.

It will be obvious to those skilled in the art that in some instances the reactions described in Methods A to H cannot be effected in the presence of reactive intermediates incompatible with the reaction conditions. In such cases, the reactive substituent must first be derivatized via known per se methods to contain a suitable protective group, which can then be subsequently removed.

Biological Properties

The above described compounds of formula 1 possess inhibitory activity against HIV-1 reverse transcriptase. By inhibiting HIV-1 reverse transcriptase, they ultimately inhibit or suppress the ability of the virus to integrate its genome into the genome of potential host cells, which, in turn, inhibits or suppresses viral replication. When administered in suitable dosage forms, alone or in combination with other anti-virals, immunomodulators, antibiotics, anti-infectives, or vaccines, they are, thus, useful in the prevention or treatment of HIV-1 infection. Another aspect of the invention, therefore, is a method for preventing or treating HIV-1 infection which comprises administering to a human being, exposed to or infected by HIV-1, a prophylactically or therapeutically effective amount of a novel compound of formula 1, as described above.

As the term is used herein, infection by HIV-1 constitutes the replication of HIV-1 in a human host.

As the term is used herein, the treatment of HIV-1 infection comprises the partial or total inhibition or suppression of replication of HIV-1 in a human host in whom replication of the virus has already begun to take place.

As the term is used herein, the prevention of HIV-1 infection comprises the complete prevention of the establishment of viral replication in a human host who has been exposed to HIV-1 but in whom replication of the virus has not yet begun to take place.

The compounds of the present invention are effective agents for the treatment of HIV-1 infection by virtue of their ability to partially or totally inhibit or suppress replication of HIV-1 in an infected human host.

When used to treat HIV-1 infection, the compounds of the present invention can be administered either before or after the onset of clinical manifestations of HIV-1 infection, such as ARC or AIDS.

The compounds of the present invention are effective for the prevention of HIV-1 infection in humans, by virtue of their ability to prevent the establishment of viral replication in a human host who has been exposed to HIV-1 but in whom replication of the virus has not yet begun to take place.

The compounds of formula 1 may be administered in single or divided doses by the oral, parenteral or topical routes. A suitable oral dosage for a compound of formula 1 would be in the range of about 100 mg to 3 g per day. A preferred oral dosage for a compound of formula 1 would be the maximum tolerated dose, which would typically be in the range of between about 200 mg and 2 g per day. In parenteral formulations, a suitable dosage unit may contain from 0.1 to 250 mg of said compounds, preferably 1 mg to 200 mg, whereas for topical administration, formulations containing 0.01 to 1% active ingredient are preferred. It should be understood, however, that the dosage administration from patient to patient will vary and the dosage for any particular patient will depend upon the clinician's judgement, who will use as criteria for fixing a proper dosage the size and condition of the patient as well as the patient's response to the drug.

When the compounds of the present invention are to be administered by the oral route, they may be administered as medicaments in the form of pharmaceutical preparations which contain them in association with a compatible pharmaceutical carrier material. Such carrier material can be an inert organic or inorganic carrier material suitable for oral administration. Examples of such carrier materials are water, gelatin, talc, starch, magnesium stearate, gum arabic, vegetable oils, polyalkylene-glycols, petroleum jelly and the like.

The pharmaceutical preparations can be prepared in a conventional manner and finished dosage forms can be solid dosage forms, for example, tablets, dragees, capsules, and the like, or liquid dosage forms, for example solutions, suspensions, emulsions and the like. The pharmaceutical preparations may be subjected to conventional pharmaceutical operations such as sterilization. Further, the pharmaceutical preparations may contain conventional adjuvants such as preservatives, stabilizers, emulsifiers, flavor-improvers, wetting agents, buffers, salts for varying the osmotic pressure and the like. Solid carrier material which can be used include, for example, starch, lactose, mannitol, methyl cellulose, microcrystalline cellulose, talc, silica, dibasic calcium phosphate, and high molecular weight polymers (such as polyethylene glycol).

For parenteral use, a compound of formula 1 can be administered in an aqueous or non-aqueous solution, suspension or emulsion in a pharmaceutically acceptable oil or a mixture of liquids, which may contain bacteriostatic agents, antioxidants, preservatives, buffers or other solutes to render the solution isotonic with the blood, thickening agents, suspending agents or other pharmaceutically acceptable additives. Additives of this type include, for example, tartrate, citrate and acetate buffers, ethanol, propylene glycol, polyethylene glycol, complex formers (such as EDTA), antioxidants (such as sodium bisulfite, sodium metabisulfite, and ascorbic acid), high molecular weight polymers (such as liquid polyethylene oxides) for viscosity regulation and polyethylene derivatives of sorbitol anhydrides. Preservatives may also be added if necessary, such as benzoic acid, methyl or propyl paraben, benzalkonium chloride and other quaternary ammonium compounds.

The compounds of this invention may also be administered as solutions for nasal application and may contain in addition to the compounds of this invention suitable buffers, tonicity adjusters, microbial preservatives, antioxidants and viscosity-increasing agents in an aqueous vehicle. Examples of agents used to increase viscosity are polyvinyl alcohol, cellulose derivatives, polyvinylpyrrolidone, polysorbates or glycerin. Microbial preservatives added may include benzalkonium chloride, thimerosal, chloro-butanol or phenylethyl alcohol.

Additionally, the compounds provided by the invention can be administered by suppository.

The compounds of the invention may be administered either alone or in combination with other anti-virals, immunomodulators, antibiotics, anti-infectives, or vaccines. For example the compounds of the invention may be administered in combination with one or more of the known nucleoside analog HIV reverse transcriptase inhibitors, such as AZT, ddI and ddC, other non-nucleoside HIV reverse transcriptase inhibitors, or HIV protease inhibitors.

As stated before, the compounds provided by the invention inhibit the enzymatic activity of HIV-1 RT. Based upon testing of these compounds, as described below, it is known that they inhibit the RNA-dependent DNA polymerase activity of HIV-1 RT. It is known (data not shown) that they also inhibit the DNA-dependent DNA polymerase activity of HIV-1 RT.

Utilizing the Reverse Transcriptase (RT) Assay described below, compounds can be tested for their ability to inhibit the RNA-dependent DNA polymerase activity of HIV-1 RT. Certain specific compounds described in the Examples which appear below, were so tested. The results of this testing appear in Table I, below.

REVERSE TRANSCRIPTASE (RT) ASSAYS

Assay Theory

Among the enzymes for which Human Immunodeficiency Virus (HIV-1) encodes is a reverse transcriptase (1), so-named because it transcribes a DNA copy from an RNA template. This activity can be quantitatively measured in a cell-free enzyme assay, which has been previously described (2), and is based upon the observation that reverse transcriptase is able to use a synthetic template [poly r(C) primed with oligo d(G)] to transcribe a radio-labelled, acid-precipitable DNA strand utilizing $^3$H-dGTP as a substrate. The assay described below utilizes the wild type (WT) enzyme, which is the predominant form of the enzyme observed in patients infected with HIV-1. Utilization of mutant RT enzymes (Y181C and Y181L, prepared by site-directed mutagenesis in which the tyrosine residue at codon 181 has been replaced by a cysteine or a leucine residue, respectively) and analogous assay conditions allows compounds to be evaluated for their effectiveness at inhibiting these mutant enzymes.

Materials a) Preparation of the wild type enzyme

Reverse transcriptase enzyme from the LAV strain of Human Immunodeficiency Virus (HIV-1) (1) was isolated from the bacterial strain JM109 (3) expressing the DNA clone pBRTprtl+ (2) which is under the control of the lac promotor in the expression vector pIBI21 (4). An overnight culture grown in 2×YT medium (37° C., 225 rpm) (5) supplemented with 100 μg/mL ampicillin for positive selection is inoculated at a 1:40 dilution into M9 medium supplemented with 10 μg/mL thiamine, 0.5% casamino acids, and 50 μg/mL ampicillin (5). The culture is incubated (37° C., 225 rpm) until it reaches an OD540 of 0.3–0.4. At that time the repressor inhibitor IPTG (isopropyl β-D-thiogalactopyranoside) is added to 0.5 mM, and the mixture is incubated for 2 additional hours. Bacteria are pelleted, resuspended in a 50 mM Tris, 0.6 mM EDTA, 0.375M NaCl buffer and digested by the addition of lysozyme (1 mg/mL) for 30 minutes on ice. The cells are lysed by the addition of 0.2% NP-40 and brought to 1M NaCl.

After removal of the insoluble debris by centrifugation, the protein is precipitated by the addition of 3 volumes of saturated aqueous ammonium sulfate. The enzyme is pelleted, resuspended in RT buffer (50 mM Tris pH 7.5, 1 mM EDTA, 5 mM DTT, 0.1% NP-40, 0.1M NaCl, and 50% glycerol), and stored at −70° C. for further use.

b) Composition of 2× concentrated stock reaction mixture

| Stock Reagent | 2X Mix Concentration |
|---|---|
| 1M Tris pH 7.4 | 100 mM |
| 1M Dithiothrietol | 40 mM |
| 1M NaCl | 012 mM |
| 1% Nonidet P-40 | 0.1% |
| 1M MgCl | 4 mM |
| [poly r(C)/oligo d(G)](5:1) | 2 μg/mL |
| $^3$H-dGTP (8 μM) | 0.6 μM |

Assay Procedure

The 2× concentrated stock reaction mixture is aliquoted and stored at −20° C. The mixture is stable and thawed for use in each assay. This enzyme assay has been adapted to a 96 well microtiter plate system, and has been previously described (6). Tris buffer (50 mM, pH 7.4), vehicle (solvent diluted to match the compound dilution), or compounds in vehicle are dispensed into 96-well microtiter plates (10 μL/well; 3 wells/ compound). The HIV-1 RT enzyme is thawed, diluted in 50 mM Tris pH 7.4 so that fifteen μL of diluted enzyme contain 0.001 Unit (one unit is that amount of enzyme to transform 1 micromole of substrate per minute at 25° C.), and fifteen μL are dispensed per well. Twenty μL of 0.12–0.5M EDTA are added to the first three wells of the microtiter plate. EDTA chelates the Mg$^{++}$ present and prevents reverse transcription. This group serves as background polymerization which is subtracted from all other groups. Twenty-five ul of the 2× reaction mixture are added to all wells and the assay is allowed to incubate at room temperature for 60 minutes. The assay is terminated by precipitating the DNA in each well with 50 μL of 10% trichloracetic acid (TCA) (10% w/v) in sodium pyrophosphate (1% w/v). The microtiter plate is incubated for 15 minutes at 4° C. and the precipitate is fixed onto #30 glass fiber paper (Schleicher & Schuell) using a Skatron semi-automatic harvester. The filters are then washed with additional TCA (5%) containing sodium pyrophosphate (1%), rinsed with aqueous ethanol (70%), dried, and transferred to scintillation vials (6). Each vial receives 2 mL of scintillation cocktail and is counted in a Beckman beta counter. The calculation for percent inhibition is as follows:

% inhibition =

$$\frac{CPM \text{ Mean Test Value} - CPM \text{ Mean Control Value} \times 100}{CPM \text{ Mean Control Value}}$$

REFERENCES

1. Benn, S., et al., *Science* 230:949, 1985
2. Farmerie, W. G. et. al., *Science* 236:305, 1987
3. Yanisch-Perron, C., Viera, J., and Messing, J., *Gene* 33:103, 1985
4. International Biotechnologies, Inc., New Haven, Conn. 06535
5. Maniatis, T., Fritsch, E. F., and J. Sambrook, eds. *Molecular Cloning: A Laboratory Manual*, Cold Spring Harbor Laboratory, 1982
6. Spira, T., et. al. *J. Clinical Microbiology*, 25:97, 1987.

In order to confirm that compounds which are active in the RT Assay also have the ability to inhibit HIV replication in a living system, compounds according to the invention were also tested in the human T-Cell Culture (Syncytia) Assay described below. The results of this testing appear in Table I.

SYNCYTIA (HUMAN T-CELL CULTURE) ASSAY

Assay Theory

Formation of syncytia is a feature of in vitro cultures of CD4+ T-cells infected with HIV-1. In this assay, T-cells are treated with a putative replication inhibiting compound and then infected with HIV-1. After incubation, the culture is checked for the formation of syncytia. The absence or reduction in the number of syncytia is used as a measure of the test compound's ability to inhibit HIV replication.

Assay Method

The target cells, designated c8166, are a subclone of human lymphoma cells of T-cell origin and are established at an initial density of $5 \times 10^4$ per 100 ul in RPMI 1640 (+10% fetal bovine serum) culture medium in 96 well flat bottom plates. A selected amount of test compound, dissolved in DMSO, is included. After 24 hours, 50–100 $TCID_{50}$'s (the dose that results in induced effect in 50% of test cultures) of the HTLV-IIIB strain of HIV-1 (2) are inoculated into each culture. Control cultures receive compound or virus only. Four days after virus challenge, cultures are visually examined for the frequency and distribution of virus-induced giant cell syncytia. The percent inhibition by the test compound is determined by comparison with control values. Confirmation of the presence or absence of virus replication is accomplished by harvesting the cell free culture fluids from all experimental groups to determine the presence or absence of infectious progeny through the induction of syncytia formation in secondary human T-cell cultures after 3 days.

REFERENCES (1) M. Somasundaran and H. L. Robinson, *Science* 242, 1554(1988).
(2) G. M. Shaw, R. H. Hahn, S. K. Arya, J. E. Groopman, R. C. Gallo and F. Wong-Staal, *Science*, 226 1165 (1984)

In order to assess the specificity of the enzyme inhibitory activity of the compounds provided by the invention, a few were tested, using known per se assay methods, for their ability to inhibit Feline Leukemia Virus-derived reverse transcriptase and Calf Thymus-derived DNA alpha-polymerase. None of the compounds so tested was observed to possess any inhibitory activity against these enzymes. These results indicate that the enzyme inhibitory activity of the compounds provided by the invention is directed rather specifically against HIV-1 RT.

In order to roughly assess the cytotoxicity of the compounds provided by the invention, several such compounds were tested in the MTT Assay described below. The results of this testing are reported in Table I, below. Compounds having a relatively high $CC_{50}$ are preferred.

MTT ASSAY

Assay Theory

The MTT [3-(4,5-dimethylthiazol-2-yl)-2,5 diphenyl tetrazolium bromide) assay is based on cleavage of tetrazolium bromide by metabolically active cells, resulting in a highly quantitative blue color. This assay has been previously described (1) but has been optimized for the purposes of the testing reported herein.

Assay Method

The H9 cell line (2), an established human lymphoma suspension cell line grown in RPMI 1640 supplemented with 10% fetal bovine serum, is used as the target cell line in the assay. Cells (100 $\mu$L) are plated in microtest plate wells at a concentration of $10^5$ cells per mL in the presence of varying concentrations of inhibitor. The cells are incubated at 37° C. in a humidified $CO_2$ incubator. Five days later, 20 $\mu$L of MTT (5 mg/mL in RPMI 1640, sonicated, 0.2 micron filtered, and stored at 4° C.) is added to each well. After 4 hours additional incubation at 37° C., 60 $\mu$L of Triton-X is added to each well and thoroughly mixed to aid the solubilization of the crystals. Absolute ethanol (5 $\mu$L) is added to each well and the resulting mixture is incubated for 30 minutes at 60° C. and immediately read on a plate reader (Dynatech) at a wavelength of 570 nm.

Data from this assay are used to generate a nonlinear regression analysis which yields an $CC_{50}$.

REFERENCES

1. Mosmann, Tim, *J. Immunol.* Methods, 65:55, 1983.
2. Jacobs, J. P., *J. Natl. Cancer Inst.*, 34:231, 1965.

TABLE I

| Compound of | Reverse Transcriptase Assay % inhibition (1 $\mu$M) | | | Syncytia Assay | MTT Assay |
|---|---|---|---|---|---|
| Example No | WT | Y181C | Y188L | $IC_{50}$ ($\mu$M) | $CC_{50}$ ($\mu$M) |
| 1 | 97 | 96 | 77 | 0.04 | >60 |
| 2 | 67 | 72 | 13 | NT | >60 |
| 3 | 63 | 36 | 24 | NT | NT |
| 4 | 60 | 54 | 29 | NT | >60 |
| 5 | 90 | 90 | 63 | NT | >60 |
| 6 | 94 | 87 | 84 | 0.01 | >60 |
| 7 | 94 | 84 | 52 | NT | NT |
| 8 | 96 | 80 | 80 | NT | NT |
| 9 | 67 | 67 | 20 | NT | NT |
| 10 | 94 | 73 | 66 | NT | NT |
| 11 | 81 | 51 | NT | NT | NT |
| 12 | 95 | 91 | 78 | 0.04 | >50 |
| 13 | 88 | 80 | 17 | 0.16 | NT |
| 14 | 74 | 51 | 23 | NT | NT |
| 15 | 52 | 59 | 10 | NT | NT |
| 16 | 83 | 74 | 34 | NT | NT |
| 17 | 78 | 62 | 27 | NT | NT |
| 18 | 87 | 82 | 57 | NT | NT |
| 19 | 91 | 75 | 55 | NT | NT |
| 20 | 65 | 36 | 26 | NT | NT |

TABLE I-continued

| Compound of Example No | Reverse Transciptase Assay % inhibition (1 μM) | | | Syncytia Assay IC$_{50}$ (μM) | MTT Assay CC$_{50}$ (μM) |
|---|---|---|---|---|---|
| | WT | Y181C | Y188L | | |
| 21 | 33 | 28 | 46 | NT | NT |
| 22 | 76 | 72 | 30 | NT | NT |
| 23 | 58 | 37 | 47 | NT | NT |
| 24 | 39 | 50 | 18 | NT | NT |
| 25 | 92 | 86 | 80 | 80 | >80 |
| 26 | 64 | 33 | 20 | NT | NT |
| 27 | 61 | 45 | 58 | NT | NT |
| 28 | 96 | 93 | 72 | NT | >15 |

EXAMPLES

The following examples further illustrate the present invention and will enable others skilled in the art to understand it more completely. It should be understood, however, that the invention is not limited to the particular examples given below. Procedures for preparing starting materials not described below may be found in copending U.S. patent application Ser. No. 08/091,418, filed on Jul. 13, 1993 or European Patent Application No. 90 121 954.3 (publication No. 0 429 987).

Example 1

5,11-Dihydro-11-ethyl-5-methyl-2-(4-pyrazolyl)-6H-dipyrido[3,2-b:2',3'-e][1,4]diazepin-6-one a) 4-(Tributylstannyl)pyrazole To a solution of 4-iodopyrazole (0.964 g) in THF (20 mL) under nitrogen and cooled to −60° C. is added t-butyllithium (1.7M in pentane, 9 mL) at such a rate that the temperature remained below −55° C. Tributyltin chloride (1.2 mL) was then added and the mixture was allowed to warm to room temperature. The reaction was quenched with water, diluted with ethyl acetate, washed with water, dried (anhyd Na$_2$SO$_4$), filtered, and evaporated. Chromatography of the residue over silica gel (ethyl acetate/hexane) gave 4-(tributylstannyl)pyrazole (0.288 g) as an oil.

b) 5,11-Dihydro-11-ethyl-5-methyl-2-(4-pyrazolyl)-6H-dipyrido[3,2-b:2',3'-e][1,4]diazepin-6-one A mixture of 4-(tributylstannyl)pyrazole (0.270 g), 5,11-dihydro-11-ethyl-5-methyl-2-trifluoromethanesulfonyloxy-6H-dipyrido[3,2-b:2',3'-e][1,4]diazepin-6-one (0.292 g), LiCl (0.157 g), and Pd(PPh$_3$)$_2$Cl$_2$ (0.034 g) in DMF (2 mL) was heated in a sealed tube at 130° C. for 15.5 h. The mixture was cooled to room temperature and stirred for 2 h with aqueous potassium fluoride. The mixture was diluted with ethyl acetate, washed with water, dried (anhyd Na$_2$SO$_4$) filtered, and evaporated. The residue was fractionated over silica gel (ethyl acetate/hexane gradient) to give the title compound, which crystallized from ethyl acetate/isopropyl ether, mp 194°–196° C.

Example 2

5,11-Dihydro-11-ethyl-2-(1-ethylpyrazol-4-yl)-5-methyl-6H-dipyrido[3,2-b:2',3'-e][1,4]diazepin-6-one The title compound (a foam, mp 60°–62° C.) was prepared from 5,11-dihydro-11-ethyl-5-methyl-2-trifluoromethanesulfonyloxy-6H-dipyrido[3,2-b:2',3'-e][1,4]diazepin-6-one and N-ethyl-4-iodopyrazole in a manner analogous to that described in Example 1.

Example 3

5,11-Dihydro-11-ethyl-5-methyl-2-(1-methylpyrazol-4-yl)-6H-dipyrido[3,2-b:2',3'-e][1,4]diazepin-6-one The title compound (mp 65°–67° C.) was prepared from 5,11-dihydro-11-ethyl-5-methyl-2-trifluoromethanesulfonyloxy-6H-dipyrido[3,2-b:2',3'-e][1,4]diazepin-6-one and N-methyl-4-iodopyrazole in a manner analogous to that described in Example 1.

Example 4

5,11-Dihydro-11-n-propyl-2-(4-pyrazolyl)-6H-dipyrido[3,2-b:2',3'-e][1,4]diazepin-6-one The title compound (mp 291°–292° C.) was prepared from 5,11-dihydro-11-n-propyl-2-trifluoromethanesulfonyloxy-6H-dipyrido[3,2-b:2',3'-e][1,4]diazepin-6-one and 4-(tributylstannyl)pyrazole in a manner analogous to that described in Example 1.

Example 5

5,11-Dihydro-5-methyl-11-n-propyl-2-(4-pyrazolyl)-6H-dipyrido[3,2-b:2',3'-e][1,4]diazepin-6-one The title compound (mp 206°–207° C.) was prepared from 5,11-dihydro-5-methyl-11-n-propyl-2-trifluoromethanesulfonyloxy-6H-dipyrido[3,2-b:2',3'-e][1,4]diazepin-6-one and 4-stannyl)pyrazole in a manner analogous to that described in Example 1.

Example 6

5,11-Dihydro-5-methyl-11-c-propyl-2-(4-pyrazolyl)-6H-dipyrido[3,2-b:2',3'-e][1,4]diazepin-6-one The title compound (mp 233°–235° C.) was prepared from 5,11-dihydro-5-methyl-11-c-propyl-2-trifluoromethanesulfonyloxy-6H-dipyrido[3,2-b:2',3'-e][1,4]diazepin-6-one and 4-stannyl)pyrazole in a manner analogous to that described in Example 1.

Example 7

2-(1-Carbamylpyrazol-3-yl)-5,11-dihydro-11-ethyl-5-methyl-6H-dipyrido[3,2-b:2',3'-e][1,4]diazepin-6-one To a solution of 5,11-dihydro-11-ethyl-5-methyl-2-(4-pyrazolyl)-6H-dipyrido[3,2-b:2',3'-e][1,4]diazepin-6-one (0.054 g) in chloroform (5 mL) was added triphosgene (0.050 g) and diisopropylethylamine (0.2 g). The mixture was stirred at room temperature for 4 days. Concentrated ammonium hydroxide (10 drops) was then added and the mixture was stirred for 10 min. The mixture was diluted with chloroform, washed with water, dried (anhyd Na$_2$SO$_4$), filtered, and evaporated. The residue was chromatographed over silica gel (ethyl acetate/ethanol) to give the title compound, which crystallized from ethyl acetate/isopropyl ether, mp 175°–180° C.

Example 8

2-(1-Acetylpyrazol-4-yl)-5,11-dihydro-11-ethyl-5-methyl-6H-dipyrido[3,2-b:2',3'-e][1,4]diazepin-6-one The title compound (mp 186°–188° C.) was prepared from 5,11-dihydro-11-ethyl-5-methyl-2-(4-pyrazolyl)-6H- dipyrido[3,2-b:2',3'-e][1,4]diazepin-6-one by heating in acetic anhydride under reflux for 1 hour in the presence of potassium acetate.

Example 9

5,11-Dihydro-11-ethyl-5-methyl-2-(3-pyrazolyl)-6H-dipyrido[3,2-b:2,'3'-e][1,4]diazepin-6-one A mixture of 5,11-dihydro-[1-(N,N-dimethylaminosulfonyl)pyrrazol-5-yl]-11-ethyl-5-methyl-6H-dipyrido[3,2-b:2',3'-e][1,4]diazepin-6-one (0.051 g) and hydrazine hydrate (0.41 g) in ethanol (0.5 mL) was stirred at reflux for 3 days. The cooled mixture was diluted with ethyl acetate, washed with water, dried (anhyd NaSO$_4$), filtered, and evaporated. The residue was fractionated by preparative plate chromatography (ethyl acetate/hexane) to give 0.020 g of the title compound as a foam.

Example 10

5,11-Dihydro-11-ethyl-5-methyl-2-(3-methylpyrazol-4-yl)-6H-dipyrido[3,2-b:2',3'-e][1,4]diazepin-6-one The title compound (mp 113°–115° C.) was prepared from 5,11-dihydro-11-ethyl-5-methyl-2-trifluoromethanesulfonyloxy-6H-dipyrido[3,2-b:2',3'-e][1,4]diazepin-6-one and 3-methyl-4-(tributylstannyl)pyrazole in a manner analogous to that described in Example 1.

Example 11

5,11-Dihydro-11-ethyl-5-methyl-2-(1-methylpyrrol-2-yl)-6H-dipyrido[3,2-b:2',3'-e][1,4]diazepin-6-one a) (1-Methylpyrrol-2-yl)tributyltin 1-Methylpyrrole (0.065 g) was added to a cooled (−35° C.), stirred solution of butyllithium (2.5M, 0.32 mL) in dry THF (5 mL). N,N,N',N'-Tetramethylethylenediamine (0.090 g) was then added and the mixture was stirred for 90 min at −10° to −15° C. Tributyltin chloride (0.26 g) was then slowly added, and the mixture was allowed to warm to room temperature and stirred for 15 min. The solvent was evaporated to provide (1-methylpyrrol-2-yl)tributyltin, suitable for use in the next reaction.

b) 5,11-Dihydro-11-ethyl-5-methyl-2-(1-methylpyrrol-2-yl)-6H-dipyrido[3,2-b:2',3'-e][1,4]diazepin-6-one A mixture of the (1-methylpyrrol-2-yl)tributyltin obtained above, 5,11-dihydro-11-ethyl-5-methyl-2-trifluoromethanesulfonyloxy-6H-dipyrido[3,2-b:2',3'-e][1,4]diazepin-6-one (0.20 g), Pd(PPh$_3$)$_2$Cl$_2$ (0.010 g), LiCl (0.100 g), and dry DMF (5 mL) was stirred at 90° C. for 15 min. After cooling to room temperature, the mixture was diluted with water, extracted with CH$_2$Cl$_2$, dried (anhyd MgSO$_4$), filtered, and concentrated. The residue was first chromatographed on a silica gel column using ethyl acetate/hexanes (1:4), and then ethyl acetate/hexanes (1:1) to give a mixture of two products. A final purification using a preparative plate chromatography (ethyl acetate/hexanes, 1:1) provided 0.025 g of the title compound as a foam, mp >60° C.

Example 12

5,11-Dihydro-11-ethyl-5-methyl-2-(3-pyrrolyl)-6H-dipyrido[3,2-b:2',3'-e][1,4]diazepin-6-one a) 3-Bromo-1-(triisopropylsilyl)pyrrole NBS (6.4 g) was added in one portion to a stirred solution of 1-(triisopropylsilyl)pyrrole (8.00 g) in dry THF (80 mL) at −78° C. The mixture was stirred at this temperature for 2 h, and was then allowed to warm to room temperature overnight. The solvent was removed, water was added to the residue, and the product extracted with CH$_2$Cl$_2$, dried (anhyd Na$_2$SO$_4$), filtered, and evaporated. The residue was chromatographed over silica gel (hexanes) and concentrated to provide 10.00 g of 3-bromo-1-(triisopropylsilyl)pyrrole as a colorless oil.

b) [1-(Triisopropylsilyl)pyrrol-3-yl]tributyltin was prepared in a manner analogous to that described in Example 16.

c) 5,11-Dihydro-11-ethyl-5-methyl-2-[1-(triisopropylsilyl)pyrrol-3-yl]-6H-dipyrido[3,2-b:2',3'-e][1,4]diazepin-6-one was prepared in a manner analogous to that described in Example 16.

d) 5,11-Dihydro-1-ethyl-5-methyl-2-(3-pyrrolyl)-6H-dipyrido[3,2-b:2',3'-e][1,4]diazepin-6-one Tetrabutylammonium fluoride in THF (1M, 0.36 mL) was added to a solution of 5,11-dihydro-1-ethyl-5-methyl-2-[1-(triisopropylsilyl)pyrrol-3-yl]-6H-dipyrido[3,2-b:2',3'-e][1,4]diazepin-6-one (0.17 g) in dry THF (10 mL). After stirring the resulting mixture for 1 h, it was diluted with ether, washed with water, dried (anhyd Na$_2$SO$_4$), filtered, and evaporated. The residue was chromatographed over silica gel (ethyl acetate/hexanes, 1:1), and then crystallized from chloroform/hexanes to give 0.083 g of the title compound, mp 173°–174° C.

Example 13

5,11-Dihydro-11-ethyl-5-methyl-2-(2-pyrrolyl)-6H-dipyrido[3,2-b:2',3'-e][1,4]diazepin-6-one a) (1-(t-Butoxycarbonyl)pyrrol-2-yl)tributyltin LDA in dry THF (1.2M, 0.83 mL) was slowly added to a cooled (−78° C.) solution of 1-(t-butoxycarbonyl)pyrrole (0.67 g) in dry THF (5 mL). After stirring for 3 h, tributyltin chloride (0.65 g) was slowly added, and the mixture was allowed to warm to room temperature overnight. The solvent was removed to provide (1-(t-butoxycarbonyl)pyrrol-2-yl)tributyltin, suitable for use in the next reaction.

b) A mixture of 5,11-dihydro-11-ethyl-5-methyl-2-trifluoromethanesulfonyloxy-6H-dipyrido[3,2-b:2',3'-e][1,4]diazepin-6-one (0.2 g), the (1-(t-butoxycarbonyl)pyrrol-2-yl)tributyltin obtained above, Pd(PPh$_3$)$_4$ (0.065 g), LiCl (0.127 g), and dry dioxane (8 mL) was refluxed for 4 h. The solvent was then evaporated, and the residue was dissolved in CH$_2$Cl$_2$, washed with water, dried (anhyd Na$_2$SO$_4$), filtered, and evaporated. The residue was chromatographed over silica gel (ethyl acetate/hexanes, 1:1), and then crystallized from ethyl acetate/hexanes. The BOC group was removed by stirring the condensation product for 30 min with HCl/ether. The solvent was evaporated and the residue purified by preparative plate chromatography (ethyl acetate/hexanes, 1:4) to give 0.022 g of the title compound as a foam, mp >60° C.

Example 14

2-(1-Acetylpyrrol-2-yl)-5,11-dihydro-11-ethyl-5-methyl-6H-dipyrido[3,2-b:2',3'-e][1,4]diazepin-6-one Sodium hydride (0.013 g, 60% in oil) was added to a solution of 5,11-dihydro-11-ethyl-5-methyl-2-(2-pyrrolyl)-6H-dipyrido[3,2-b:2',3'-e][1,4]diazepin-6-one (0.100 g) in dry DMF (3 mL) and stirred for 30 min. After cooling to 0° C., acetyl chloride (0.025 g) was added and the reaction mixture was allowed to warm to room temperature overnight. Water was added and the product was extracted with $CH_2Cl_2$, dried (anhyd $Na_2SO_4$), filtered, and evaporated. The residue was purified by preparative plate chromatography (ethyl acetate/hexanes, 1:1). Crystallization from ethyl acetate/pet ether gave 0.018 g of the title compound, mp 106°–108° C.

Example 15

2-(2-Acetylpyrrol-3-yl)-5,11-dihydro-11-ethyl-5-methyl-6H-dipyrido[3,2-b:2',3'-e][1,4]diazepin-6-one mp >80° C.

Phosphorus oxychloride (0.054 g) was added to cooled (10° C.) dry N,N-dimethylacetamide (0.031 g), and the mixture was stirred 15 min after removal of the cold bath. Dichloroethane (2 mL) was added and the resulting mixture cooled to 5° C. 5,11-Dihydro-11-ethyl-5-methyl-2-(3-pyrrolyl)-6H-dipyrido[3,2-b:2',3'-e][1,4]diazepin-6-one (0.10 g) in dichloroethane (5 mL) was added over 10 min, and the cold bath was removed and the mixture heated at reflux for 3 h. After cooling to room temperature, the mixture was poured into excess aqueous sodium acetate and stirred for 2 h. The product was extracted with $CH_2Cl_2$, dried (anhyd $Na_2SO_4$), filtered, and evaporated. The residue was purified by preparative plate chromatography (ether) to give 0.014 g of the title compound as a foam, mp>80° C. Also isolated was 0.038 g of 2-(2-acetylpyrrol-4-yl)-5,11-dihydro-11-ethyl-5-methyl-6H-dipyrido[3,2-b:2',3'-e][1,4]diazepin-6-one (Example 17), mp 219°–220° C.

Example 16

5,11-Dihydro-2-[2-(ethoxycarbonyl)pyrrol-4-yl]-11-ethyl-5-methyl-6H-dipyrido[3,2-b:2',3'-e][1,4diazepin-6-one a) Trichloroacetyl chloride (0.114 g) was added to a solution of 5,11-dihydro-11-ethyl-5-methyl-2-(3-pyrrolyl)-6H-dipyrido[3,2-b:2',3'-e][1,4]diazepin-6-one (0.052 g) in diglyme (2.5 mL), and the resulting mixture stirred at 100° C. for 2 h. The reaction mixture was then poured over ice, and the product was extracted with $CH_2Cl_2$, dried (anhyd $Na_2SO_4$), filtered, and evaporated. The residue was chromatographed over silica gel (ethyl acetate/methylene chloride, 1:9) to give 0.070 g of 5,11-dhydro-11-ethyl-5-methyl-2-[2-(trichloroacetyl)pyrrol-4-yl]-6H-dipyrido[3,2-b:2',3'-e][1,4]diazepin-6-one.

b) The product (0.065 g) from Example 16a was added to absolute ethanol (6 mL) and tri-ethylamine (0.035 g), and the resulting mixture stirred at 90° C for 10 h. Purification as in Example 16a, followed by crystallization from ethyl acetate/hexanes provided 0.048 g of the title compound, mp 209°–210° C.

Example 17

2-(2-Acetylpyrrol-4-yl)-5,11-dihydro-11-ethyl-5-methyl-6H-dipyrido[3,2-b:2',3'-e][1,4]diazepin-6-one The title compound (mp 219°–220° C.) was isolated from the reaction mixture as described in Example 20.

Example 18

2-(2-Cyanopyrrol-3-yl)-5,11-dihydro-11-ethyl-5-methyl-6H-dipyrido[3,2-b:2',3'-e][1,4]diazepin-6-one A solution of 5,11-dihydro-11-ethyl-5-methyl-2-(3-pyrrolyl)-6H-dipyrido[3,2-b:2',3'-e][1,4]diazepin-6-one (0.093 g) in DMF (1 mL) and $CH_3CN$ (1 mL) was cooled to −50° C., and chlorosulfonyl isocyanate (0.041 g) was added in one portion. The resulting mixture was allowed to warm to room temperature and stirred for 2 h, then poured into water, extracted with $CH_2Cl_2$, dried (anhyd $Na_2SO_4$), filtered, and evaporated. The residue was purified by preparative plate chromatography (ether) to give two pure compounds. Crystallization of each of these pure compounds from ethyl acetate/pet ether provided 0.038 g of the title compound, mp 262°–263° C., and 0.038 g of 2-(2-cyanopyrrol-4-yl)-5,11-dihydro-11-ethyl-5-methyl-6H-dipyrido[3,2-b:2',3'-e][1,4]diazepin-6-one, mp 268°–269° C.

Example 19

2-(2-Cyanopyrrol-4-yl)-5,11-dihydro-11-ethyl-5-methyl-6H-dipyrido[3,2-b:2',3'-e][1,4]diazepin-6-one The title compound (mp 268°–269° C.) was isolated from the reaction mixture as described in Example 18.

Example 20

5,11-Dihydro-11-ethyl-5-methyl-2-(1-methylpyrrol-3-yl)-6H-dipyrido[3,2-b:2',3'-e][1,4]diazepin-6-one Sodium hydride (0.008 g, 60% in oil) was added to a solution of 5,11-dihydro-11-ethyl-5-methyl-2-(3-pyrrolyl)-6H-dipyrido[3,2-b:2',3'-e][1,4]diazepin-6-one (0.065 g) in dry DMF (3 mL) and stirred for 30 min. Methyl iodide (0.2 mL) was added and the reaction mixture was stirred for an additional 2 h. Water was added and the product was extracted with $CH_2Cl_2$, dried (anhyd $Na_2SO_4$), filtered, and evaporated. The residue was chromatographed over silica gel (ethyl acetate/hexanes, 1:1) and was further purified by preparative plate chromatography (ethyl acetate/hexanes, 1:1) to give 0.040 g of the title compound, mp 187°–188° C.

Example 21

2-(2-Carboxypyrrol-4-yl)-5,11-dihydro-11-ethyl-5-methyl-6H-dipyrido[3,2-b:2',3'-e][1,4]diazepin-6-one A mixture of 0.092 g of 5,11-dhydro-11-ethyl-5-methyl-2-[2-(trichloroacetyl)pyrrol-4-yl]-6H-dipyrido[3,2-b:2',3'-e][1,4]diazepin-6-one (Example 21a), $K_2CO_3$ (0.55 g), was stirred at 95° C. for 1.5 h. The mixture was cooled, acidified, and washed with $CH_2Cl_2$. The aqueous phase was filtered to give 0.016 g of the title compound, which was recrystallized from acetic acid/hexanes, mp 256°–257° C.

Example 22

2-(2-Carbamylpyrrol-4-yl)-5,11-dihydro-11-ethyl-5-methyl-6H-dipyrido[3,2-b:2',3'-e][1,4]diazepin-6-one A solution of 0.100 g of 5,11-dhydro-11-ethyl-5-methyl-2-[2-(trichloroacetyl)pyrrol-4-yl]-6H-dipyrido[3,2-b:2',3'-e][1,4]diazepin-6-one (Example 21a) in dry THF (15 mL) was cooled to −15° C., and ammonia gas was bubbled through the solution for 15 min. The mixture was then tightly stoppered and stirred at room temperature for 3 h. After evaporation of the solvent, water was added and the mixture was washed with $CH_2Cl_2$. The product was filtered from the aqueous phase, dried, and recrystallized from DMF/ethanol to give 0.056 g of the title compound, mp 284°–285° C.

Example 23

5,11-Dihydro-5-ethyl-11-methyl-2-(2-pyrrolyl)-6H-dipyrido[3,2-b:2',3'-e][1,4]diazepin-6-one A mixture of 2-chloro-5,11-dihydro-5-ethyl-11-methyl-6H-dipyrido[3,2-b:2',3'-e][1,4]diazepin-6-one (0.21 g), (t-butoxycarbonyl)pyrrole (0.25 g), potassium acetate (0.20 g), Pd(PPh$_3$)$_2$Cl$_2$ (0.030 g), and 1-methyl-2-pyrrolidinone (2.5 mL) were heated in a sealed tube at 140° C. for 14 h. After removing the solvent, water was added and the product was extracted with CH$_2$Cl$_2$, dried (anhyd Na$_2$SO$_4$), filtered, and evaporated. The residue was chromatographed over silica gel (ethyl acetate/methylene chloride, 1:9) and was further purified by preparative plate chromatography (ethyl acetate/methylene chloride, 1:9) to give, after recrystallization from ethyl acetate/hexanes, 0.020 g of the title compound, mp 161°–162° C.

Example 24

5,11-Dihydro-5,11-dimethyl-2-(2-pyrrolyl)-6H-dipyrido[3,2-b:2',3'-e][1,4]diazepin-6-one The title compound (mp 158°–160° C.) was prepared from 2-chloro-5,11-dihydro-5,11-dimethyl-6H-dipyrido[3,2-b:2',3'-e][1,4]diazepin-6-one and (t-butoxycarbonyl)pyrrole in a manner analogous to that described in Example 23.

Example 25

11-Cyclopropyl-5,11-dihydro-5-methyl-2-(3-pyrrolyl-6H-dipyrido[3,2-b:2',3'-e][1,4]diazepin-6-one The title compound (mp 254°–255° C.) was prepared from 11-cyclopropyl-5,11-dihydro-5-methyl-2-trifluoromethanesulfonyloxy-6H-dipyrido[3,2-b:2',3'-e][1,4]diazepin-6-one and (triiso-propylsilyl)pyrrol-3-yl]tributyltin in a manner analogous to that described in Examples 17 and 16.

The compounds of the following examples were made in an analogous manner to those described above, or by obvious modifications thereof.

Example 26

5,11-Dihydro-11-ethyl-5-methyl-2-(4-pyrazolyl)-6H-dipyrido[3,3-b:2',3'-e][1,4]diazepin-6-one, mp 213°–214° C.

Example 27

5,11-Dihydro-11-ethyl-2-(5-methoxyindol-2-yl)-5-methyl-6H-dipyrido[3,2-b:2',3'-e][1,4]diazepin-6-one, mp 234.5°–235.5° C.

Example 28

5,11-Dihydro-11-ethyl-2-(indol-3-yl)-5-methyl-6H-dipyrido[3,2-b:2',3'-e][1,4]diazepin-6-one, mp 241°–241.5° C.

| Example A Capsules or Tablets | | | |
|---|---|---|---|
| A-1 | | A-2 | |
| Ingredients | Quantity | Ingredients | Quantity |
| Compound of Ex. 12 | 250 mg | Compound of Ex. 12 | 50 mg |
| Starch | 160 mg | Dicalcium Phosphate | 160 mg |
| Microcrys. Cellulose | 90 mg | Microcrys. Cellulose | 90 mg |
| Na Starch Glycolate | 10 mg | Stearic acid | 5 mg |
| Magnesium Stearate | 2 mg | Sodium Starch Glycolate | 10 mg |
| Fumed colloidal silica | 1 mg | Fumed colloidal silica | 1 mg |

The compound of Example 12 is blended into a powder mixture with the premixed excipient materials as identified above with the exception of the lubricant. The lubricant is then blended in and the resulting blend compressed into tablets or filled into hard gelatin capsules.

| EXAMPLE B Parenteral Solutions | |
|---|---|
| Ingredients | Quantity |
| Compound of Example 12 | 500 mg |
| Tartaric acid | 1.5 g |
| Benzyl Alcohol | 0.1% by weight |
| Water for injection | q.s. to 100 mL |

The excipient materials are mixed with the water and thereafter the compound of Example 12 is added. Mixing is continued until the solution is clear. The pH of this solution is adjusted to 3.0 and is then filtered into the appropriate vials or ampoules and sterilized by autoclaving.

| EXAMPLE C Nasal Solutions | |
|---|---|
| Ingredients | Quantity |
| Compound of Example 12 | 100 mg |
| Citric acid | 1.92 g |
| Benzalkonium chloride | 0.025% by weight |
| EDTA | 0.1% by weight |
| Polyvinylalcohol | 10% by weight |
| Water | q.s. to 100 mL |

The excipient materials are mixed with the water and thereafter the compound of Example 12 is added and mixing is continued until the solution is clear. The pH of this solution is adjusted to 4.0 and is then filtered into the appropriate vials or ampoules.

We claim:

1. A compound of the formula 1

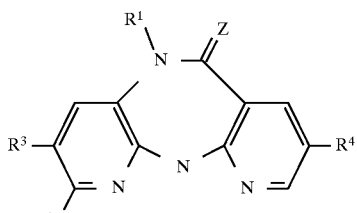

wherein,

Z is an oxygen or sulfur atom, =NCN or a group of the formula =NOR$^{10}$ wherein R$^{10}$ is alkyl of 1 to 3 carbon atoms;

R$^1$ is a hydrogen atom, alkyl of 1 to 3 carbon atoms, fluoroalkyl of 1 to 3 carbon atoms and 1 to 3 fluorine atoms, cyclopropyl, allyl, propargyl, 2-halo-2-propen-1-yl, mono- or dihalovinyl, alkanoyl or alkyl (thiocarbonyl) of 2 to 3 carbon atoms, alkylsulfonyl of 1 to 2 carbon atoms, mono- or di-alkylaminocarbonyl wherein the alkyl moiety contains 1 to 2 carbon atoms, aminoethyl, mono- or di-alkylaminoethyl wherein the alkyl moiety contains 1 to 2 carbon atoms, alkyloxyalkyl or alkylthioalkyl of 2 to 3 carbon atoms, or cyanoalkyl wherein the alkyl moiety contains 1 to 2 carbon atoms;

R$^2$ is a hydrogen atom, alkyl of 1 to 4 carbon atoms, fluoroalkyl of 1 to 4 carbon atoms and 1 to 3 fluorine atoms, cycloalkyl of 3 to 6 carbon atoms, oxetanyl, thietanyl, tetrahydrofuranyl, tetrahydrothienyl, tetrahydropyranyl, tetrahydrothiopyranyl, alkenylmethyl or alkynylmethyl of 3 to 4 carbon atoms, alkyloxyalkyl or alkylthioalkyl of 2 to 3 carbon atoms, alkanoyl or alkyl(thiocarbonyl) of 2 to 5 carbon atoms, or cyanoalkyl of 2 to 3 carbon atoms;

$R^3$ is a hydrogen atom, methyl or a halogen atom;

$R^4$ is a hydrogen atom, hydroxy, amino, hydroxymethyl, or aminomethyl; and,

Ar is a group of the formula I, II, III, IV or V

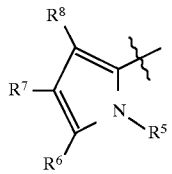
I

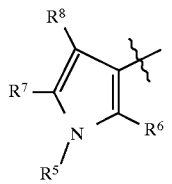
II

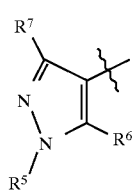
III

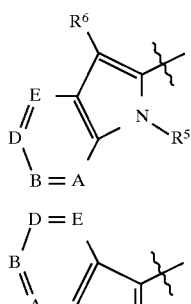
IV

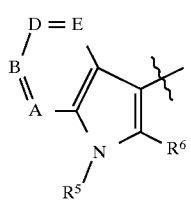
V wherein, $R^5$ is hydrogen, methyl, ethyl, acetyl, aminocarbonyl, (N-alkyl)aminocarbonyl, or (N,N-dialkyl)aminocarbonyl, wherein the alkyl moieties each contain one to two carbon atoms;

$R^6$, $R^7$ and $R^8$ are each hydrogen; or, one of $R^6$, $R^7$ and $R^8$ is methyl, ethyl, hydroxymethyl, hydroxyethyl, trifluoromethyl, halogen, acetyl, methoxycarbonyl, ethoxycarbonyl, carboxy, mono- or dimethylaminosulfonyl, aminosulfonyl, mono- or dimethylaminocarbonyl, aminocarbonyl, methyl- or ethylsulfinyl, methyl- or ethylsulfonyl, cyano, or nitro, and the remaining two substituents are both hydrogen;

A, B, D, and E are each methine groups, one of which may optionally be substituted with $R^9$; or, one of A, B, D, and E is a nitrogen atom, and the remaining three of A, B, D, and E are each methine groups, one of which methine groups may optionally be substituted with $R^9$; and, $R^9$ is alkyl or alkyloxy of 1 to 3 carbon atoms, amino, mono- or dimethylamino, hydroxyl, methylsulfonylamino, acetylamino, acetyloxy, aminocarbonyl, mono- or dimethylaminocarbonyl, or halogen;

or a pharmaceutically acceptable salt thereof.

2. A compound of formula 1, as set forth in claim 1, wherein,

Z is an oxygen or sulfur atom, or a group of the formula =$NOR^{10}$ wherein $R^{10}$ is methyl or ethyl;

$R^1$ is a hydrogen atom, alkyl of 1 to 3 carbon atoms, or allyl;

$R^2$ is alkyl of 1 to 3 carbon atoms or cycloalkyl of 3 to 4 carbon atoms;

$R^3$ is a hydrogen atom, methyl, chloro, or bromo;

$R^4$ is a hydrogen atom;

Ar is a group of the formula I, II, III, IV or V, wherein, $R^5$ is hydrogen, methyl or ethyl;

$R^6$, $R^7$ and $R^8$ are each hydrogen; or, one of $R^6$, $R^7$ and $R^8$ is methyl, ethyl, hydroxymethyl, hydroxyethyl, trifluoromethyl, halogen, acetyl, methoxycarbonyl, ethoxycarbonyl, mono- or dimethylaminosulfonyl, aminosulfonyl, mono- or dimethylaminocarbonyl, aminocarbonyl, methyl- or ethylsulfinyl, methyl- or ethylsulfonyl, cyano, or nitro, and the remaining two substituents are both hydrogen;

A, B, D, and E are each methine groups, one of which may optionally be substituted with $R^9$; or, one of A, B, D, or E is a nitrogen atom, and the remaining three of A, B, D, and E are each methine groups, one of which methine groups may optionally be substituted with $R^9$; and, $R^9$ is alkyl or alkyloxy of 1 to 3 carbon atoms, amino, hydroxyl, or halogen;

or a pharmaceutically acceptable salt thereof.

3. A compound of formula 1, as set forth in claim 1, wherein,

Z is an oxygen or sulfur atom;

$R^1$ is methyl;

$R^2$ is alkyl of 2 to 3 carbon atoms, or cycloalkyl of 3 to 4 carbon atoms;

$R^3$ and $R^4$ are each hydrogen atoms;

Ar is a group of the formula I, II or III, wherein, $R^5$ is hydrogen or methyl;

$R^6$, $R^7$ and $R^8$ are each hydrogen; or, one of $R^6$, $R^7$ and $R^8$ is methyl, trifluoromethyl, acetyl, methoxycarbonyl, ethoxycarbonyl, or cyano, and the remaining two substituents are both hydrogen; or, Ar is a group of the formula IV or V, wherein, $R^5$ is hydrogen or methyl;

$R^6$, $R^7$ and $R^8$ are each hydrogen, or one of $R^6$, $R^7$ and $R^8$ is methyl and the remaining two substituents are both hydrogen;

A, B, D, and E are each methine groups, one of which may optionally be substituted with $R^9$; or, one of A, B, D, or E is a nitrogen atom, and the remaining three of A, B, D, and E are each methine groups, one of which methine groups may optionally be substituted with $R^9$; and, $R^9$ is hydrogen, alkyl or alkyloxy of 1 to 3 carbon atoms, amino, hydroxyl, or halogen;

or a pharmaceutically acceptable salt thereof.

4. A compound selected from the group consisting of:

5,11-Dihydro-11-ethyl-5-methyl-2-(3-pyrrolyl)-6H-dipyrido[3,2-b:2',3'-e][1,4]diazepin-6-one;

11-Cyclopropyl-5,11-dihydro-5-methyl-2-(3-pyrrolyl)-6H-dipyrido[3,2-b:2',3'-e][1,4]diazepin-6-one;

11-Cyclopropyl-5,11-dihydro-5-methyl-2-(4-pyrazolyl)-6H-dipyrido[3,2-b:2',3'-e][1,4]diazepin-6-one; and, 5,11-Dihydro-11-ethyl-5-methyl-2-(4-pyrazolyl)-6H-dipyrido[3,2-b:2',3'-e][1,4]diazepin-6-one;

and the pharmaceutically acceptable salts thereof.

5. A method for inhibiting HIV-1 replication in a human host infected by HIV-1, which comprises administering to such host an amount of a compound, as set forth in claims 1, 2, 3, or 4, or a pharmaceutically acceptable salt thereof, which is sufficient to inhibit HIV-1 replication.

6. A method for treating HIV-1 infection which comprises administering, to a human being exposed to or infected by HIV-1, a therapeutically effective amount of a compound, as set forth in claims 1, 2, 3, or 4, or a pharmaceutically acceptable salt thereof.

7. A pharmaceutical composition suitable for preventing or treating HIV-1 infection which comprises a prophylactically or therapeutically effective amount of a compound, as set forth in claims 1, 2, 3, or 4, or a pharmaceutically acceptable salt thereof, and a pharmaceutically acceptable carrier.

* * * * *